United States Patent
Kang et al.

(10) Patent No.: US 6,503,530 B1
(45) Date of Patent: Jan. 7, 2003

(54) METHOD OF PREVENTING DEVELOPMENT OF SEVERE METABOLIC DERANGEMENT IN INBORN ERRORS OF METABOLISM

(76) Inventors: Chunghee Kimberly Kang, 16 Forest Gate Cir., Oak Brook, IL (US) 60523; David S. Kang, 16 Forest Gate Cir., Oak Brook, IL (US) 60523

( * ) Notice: Subject to any disclaimer, the term of this patent is extended or adjusted under 35 U.S.C. 154(b) by 0 days.

(21) Appl. No.: 10/000,204

(22) Filed: Nov. 1, 2001

(51) Int. Cl.$^7$ .............................................. A61K 47/00
(52) U.S. Cl. ............................ 424/439; 424/400; 514/2
(58) Field of Search ............................... 424/439; 514/2

(56) References Cited

U.S. PATENT DOCUMENTS

| | | | |
|---|---|---|---|
| 3,995,071 A | 11/1976 | Goodnight, Jr. et al. | 426/598 |
| 4,088,795 A | 5/1978 | Goodnight, Jr. et al. | 426/598 |
| 5,021,245 A | 6/1991 | Borschel et al. | 426/2 |
| 5,492,899 A | 2/1996 | Masor et al. | 514/47 |
| 5,550,146 A * | 8/1996 | Acosta et al. | 514/400 |
| 5,587,399 A * | 12/1996 | Acosta et al. | 424/601 |
| 5,700,590 A | 12/1997 | Masor et al. | 426/656 |
| 6,039,985 A | 3/2000 | Kamarei | 426/72 |
| 6,099,871 A | 8/2000 | Martinez | 426/2 |
| 6,136,858 A | 10/2000 | Kuchan et al. | 514/560 |
| 6,162,472 A | 12/2000 | Griffin et al. | 426/42 |
| 6,194,009 B1 | 2/2001 | Kamarel | 426/72 |
| 6,200,624 B1 | 3/2001 | Mazer et al. | 426/590 |

OTHER PUBLICATIONS

George H. Beaton, *Nutritional Needs During the First Year of Life*, Pediatric Clinics of North America, vol. 32, No. 2, Apr. 1985, 275–288.
N. Raiha et al, *Milk Protein Intake in the Term Infant*, 75 ACTA Paediatrica Scandinavica 881–886 (1986).
N. Raiha et al. *Milk Protein Intake in the Term Infant*, 75 ACTA Paedriatr Scand 887–892 (1986).
Lynn M. Janas et al., *Indices of Protein Metabolism in Term Infants Fed Either Human Milk or Formulas with Reduced Protein Concentration and Various Whey/Casein Ratios*, The Journal of Pediatrics, vol. 110, No. 6, 1987, 838–843.
Thomas A. Picone et al., *Growth, Serum Biochemistries, and Amino Acids of Term Infants Fed Formulas with Amino Acid and Protein Concentration Similar to Human Milk*, Journal of Pediatric Gastroenterology and Nutrition 9:351–360 (1989).

T.F. Fok et al., *Late Metabolic Acidosis and Poor Weight Gain in Moderately Pre–term Babies Fed with a Casein–pedominant Formula: A Continuing Need for Caution*, Annals of Tropical Paediatrics 9:243–247 (1989).
B. Lonnerdal & C.L. Chen, *Effects of Formula Proten Level and Ratio on Infant Growth, Plasma Amino Acids and Serum Trace Elements*, ACTA Paediatrica Scandinavica 7:257–265 (1990).
Samuel J. Foman, *Requirements and Recommended Dietary Intakes of Protein During Infancy*, Pediatric Research, vol. 30, No. 5, 1991, 391–395.
Niels C. Raiha et al., *Protein Nutrition During Infancy—An Update*, Pediatric Clinics of North America, vol. 42, No. 4, Aug. 1995, 745–764.
Erik Arthur Anderson & Ditlef Bucher, *Cerebrospinal Fluid Glutamine in Intracranical Hemmorhage in the Newborn*, 75 ACTA Paediatr Scand 899–904 (1986).
K. G. Dewey & B. Lonnerdal, *Infant Self–Regulation of Breast Milk Intake*, 75 ACTA Paediatr Scand 893–898 (1986).
Saul W. Brusilow & Arthur L. Horwich, The Metabolic and Molecular Bases of Inherited Disease, 1187–1231 (Charles R. Scriver et al., 7$^{th}$ed. 1995).
David T. Chuang & Vivian E. Shih, The Metabolic and Molecular Bases of Inherited Disease, 1239–1277 (Charles R. Scriver et al. eds. 7$^{th}$ed. 1995).
Wayne N. Fenton & Leon E. Rosenberg, The Metabolic and Molecular Bases of Inherited Disease, 1423–1449 (Charles R. Scriver et al. eds., 7$^{th}$ed. 1995).
American Academy of Pediatrics, Committee on Nutrition, Pediatric Nutrition Handbook, 655–659 (4$^{th}$ed. 1998).
American Academy of Pediatrics, Committee on Nutrition, Normal Childhood Nutrition & Its Disorders 99 (7$^{th}$ed. 1982).
Nelson Textbook of Pediatrics 174 (Victor C. Vaughan III et al. eds., 10$^{th}$ed. 1975).
Nelson Texbook of Pediatrics 156, 158–159 (Richard E. Behrman et al. eds., 16$^{th}$ed. W B Saunders Co. 2000).
Plyllis B. Acosta & Steven Yannicelli, The Ross Metabolic Formula System Nutrition Support Protocols 394–397 (Angeline M. Cameron ed. Ross Laboratories 1993).

* cited by examiner

*Primary Examiner*—José G. Dees
*Assistant Examiner*—Konata M. George
(74) *Attorney, Agent, or Firm*—Brinks Hofer Gilson & Lione

(57) ABSTRACT

The present invention provides a method of avoiding rapid development of extreme hyperammonemia and metabolic acidosis in undiagnosed metabolically abnormal infants having an inherited metabolic disorder.

8 Claims, No Drawings

METHOD OF PREVENTING DEVELOPMENT OF SEVERE METABOLIC DERANGEMENT IN INBORN ERRORS OF METABOLISM

BACKGROUND OF THE INVENTION

The present invention provides a method of avoiding rapid development of extreme hyperammonemia and metabolic acidosis in undiagnosed metabolically abnormal infants having an inherited metabolic disorder.

Inborn errors of metabolism occur when there is a block in a pathway in a metabolic sequence. The block results in a rapid accumulation of normal intermediary products in abnormally large amounts and also of products of usually little used metabolic pathways. This biochemical abnormality is when characterized by hyperammonemia and/or ketoacidosis in neonatal-onset metabolic disorder. Restricting the intake of the essential substance from which the toxic metabolite is derived can treat the accumulated toxic effects of these intermediary metabolites. This minimizes the accumulation of intermediates that damage organs, particularly the nervous system, and affects the extent of mental retardation.

Conventional management of infants diagnosed with certain inborn errors of amino acid or nitrogen metabolism requires the restriction of the specific amino acid(s) to the minimum amount required for normal growth and development. The amount of the restricted amino acid provided by the diet must be sufficient to meet the metabolic requirements dependent on it, but it must not permit an excess accumulation in the body fluids of the amino acid or its derivatives, or of nitrogen.

However, until the infant has been diagnosed with a metabolic disorder by newborn screening, or unless the infant is suspected of having such a disease due to a previously affected sibling, the early stage of the disease is often overlooked. During this period, referred to as the asymptomatic period, sometimes the accumulation of metabolites is extremely fast and extensive and the underlying metabolic deterioration rapidly progresses toward an abrupt onset of "intoxication-like" clinical distress. As a result the severity of metabolic insult at the discovery of disorder is often too advanced for adequate management and results in serious permanent damage of central nervous system and mental retardation.

General clinical presentation of acute metabolic disorder is essentially similar despite biochemical differences. Infantile type acute hyperammonemia and metabolic acidosis due to inborn errors of metabolism usually develop within a week of life, sometimes two to three days after birth. The infant, almost always, the product of a full-term normal pregnancy with no known prenatal or perinatal risk factors, and normal labor and delivery, appears to be normal for at least 24 hours. The onset of the illness within the first few days after birth is often fulminant with lethargy, hypotonia, vomiting, hypothermia, and hyperventilation. Without timely intervention, the infant progresses rapidly to coma and early death.

Conventional treatment of metabolic diseases caused by inborn errors of metabolism typically includes some form of dietary management, usually by consumption of a formula composed of the minimum amount essential for normal growth of one or more amino acids believed to be the basis of the disease FDA regulations specify minimum and, in some cases, maximum nutrient level requirements for infant formulas, based on recommendations by the American Academy of Pediatrics Committee on Nutrition. Human milk has long been recognized as the feeding standard for term infant feeding. Human milk comprises between about 1.3 to about 1.6 g protein per 100 kcal milk having 20 kcal/oz. Protein concentrations as low as 1.1 g protein per 100 ml of formula having 20 kcal/oz. (or 1.6 g protein per 100 kcal of formula) have provided normal growth and serum indicators of protein nutritional status. See Picone et al; *J. Pediatr Gastroenterol Nutr,* 1989; 9:351–360. The minimum amount of protein recommended by the Committee on Nutrition, American Academy of Pediatrics is 1.8 g protein per 100 kcal (or 1.2 g protein per 100 ml) formula having 20 kcal/oz.

Typical commercial formulas of 20 kcal/oz have 2.1 to 2.3 g protein per 100 kcal. See, Tables 4–5, Normal Childhood Nutrition & Its Disorders, Current Pediatric Diagnosis & Treatment, $7^{th}$ ed. (1982), p. 99 and Tables E1 and E2, Pediatric Nutrition Handbook, $4^{th}$ ed (1998), p. 655.

Table I, below, illustrates the excessive amount of protein content of several commercial formulas:

TABLE I

|  | Cal/oz (kcal/oz) | Protein g/100 ml | Protein g/100 kcal |
|---|---|---|---|
| Enfamil, Mead Johnson | 20 | 1.42 | 2.1 |
| Similac, Ross | 20 | 1.45 | 2.2 |
| SMA, Wyeth | 20 | 1.5 | 2.3 |
| Nutramigen, Mead Johnson | 20 | 1.9 | 2.8 |
| Isomil, Ross | 20 | 1.7 | 2.5 |
| ProSobee, Mead Johnson | 20 | 2.0 | 3.0 |
| Portagen, Mead Johnson | 20 | 2.2 | 3.5 |
| Progestimil, Mead Johnson | 20 | 1.9 | 2.8 |

Formula for use in the nutritional support of various inherited metabolic disorders restricts the amino acids that are responsible for the accumulation of toxic intermediary metabolites, but typically maintains the FDA recommended amount of protein. For example, U.S. Pat. No. 5,550,146 (Acosta et al.) discloses a generic powder base rich in fats, carbohydrates, vitamins, minerals and trace elements which can be readily admixed with specific amino acids to yield several different therapeutic products for use in nutritional support of various inherited metabolic diseases.

A serious problem encountered with conventional treatment is that it is typically delayed until the infant is diagnosed with such a disease. By the time the disorder is discovered, the severity of metabolic insult is often too advanced for adequate management and, in most cases, results in serious permanent damage of the central nervous system, mental retardation, coma or death.

Thus, it is highly desirable to provide a method of postponing the onset and/or substantially reducing the severity of metabolic intoxication in metabolically abnormal infants prior to diagnosis is desirable.

SUMMARY OF THE INVENTION

The method of the present invention overcomes the problems encountered in the prior art by restricting the protein intake of the general population of full-term newborns, which include normal and undiagnosed, metabolically abnormal newborns, to minimum level required for normal growth at least during the first two weeks of life until newborn screening for inherited metabolic disorders is complete.

DETAILED DESCRIPTION OF THE PREFERRED EMBODIMENTS

The present invention is drawn to a method of providing nutritional support to a patient with an inborn error of metabolism prior to detection of the inborn error and prior to development of symptoms. Neonatal-onset of inborn metabolic disorders often manifest extremely severe hyperammonemia and/or ketoacidosis leading to permanent neurologic damage unless a prompt and aggressive treatment is pursued. The present inventors have found that the severity and onset of metabolic disorders can be substantially reduced and extended, respectively after birth if the protein content of infant formulas is controlled for undiagnosed, metabolically abnormal infants during their early life.

The sudden development of extreme hyperammonemia over about 800 micromoles/dL of plasma ammonia and severe metabolic acidosis as low as blood pH below 7.0 can be avoided by reducing protein intake to a minimum level required for normal growth at least during the first two weeks of life until metabolic screening is completed.

Patients

The present invention is used to provide nutritional support that will suffice the minimum protein requirement for normal growth in human patients from birth until the time that the testing results for an inborn error of metabolism are received After birth, all full-term infants receive conventionally available formulas that contain 1.42 to 1.6 g protein per 100 ml (2.1 to 2.7 g protein per 100 kcal). If protein content is reduced to the minimum level required for normal growth, the magnitude of clinical and metabolic severity will be substantially reduced compared with the full-blown metabolic deterioration. Clinical geneticists often notice less severe clinical manifestations of metabolic disorders in breast-fed infants compared with formula-fed infants. For instance, symptoms of classic maple syrup urine disease (MSUD) normally develop between 4 to 7 days after birth, whereas breast-feeding sometimes delays onset to the second week of life. Highly restricted quantities of branched amino acids are usually required for maintaining normal plasma amino acid level in classic MSUD. Nevertheless, even the range of 30 percent reduction of protein intake seems effective to delay the onset of clinical symptoms. Hence, the reduction of protein within the range allowing normal growth of normal full-term infants can be used to lessen the severity of metabolic derangement before establishing diagnosis. Although the protein content of 1.06 g protein per 100 ml (or 1.58 g protein per 100 kcal) in mature human milk is substantially lower than conventional commercial formulas, postpartum human milk contains 2.29 g protein per 100 ml (or 3.39 g protein per 100 kcal) during the first 5 days and 159 g protein per 100 ml (or 2.35 g. protein per 100 kcal) during 6–10 days after delivery. See Table 41-1, The Feeding of Infants and Children, Nelson Textbook of Pediatrics, $16^{th}$ ed. (2000), pp. 155. New mothers, however, typically do not lactate well and the volume of intake by the breast-fed infant is much lower than the formula-fed infant. Thus, the delayed onset of clinical symptoms in breast-fed infants is suspected to be due to a reduced protein intake despite the high protein content of postpartum human milk. With breast feeding, it is difficult to adjust the amount of intake. Moreover, the amount of protein intake of either postpartum or mature human milk is highly variable in each individual. Hence, breast-feeding lacks the advantage attained by feeding the infant a calculated amount of a formula having reduced protein with normal calories and other nutrients. The estimated intake of male breast-fed infants during the first month is 2.09 g protein per kg of body weight per day. An infant weighing 3.4 kg consumes usually 630 ml of milk or formula, which suggests that 1.12 g protein per 100 ml (or 1.66 g protein per 100 kcal) of formula or milk meets this requirement.

The present invention is intended to be used to provide nutritional support for the general population of full-term newborn infants, including both normal infants and undiagnosed, metabolically abnormal infants having an inherited metabolic disorder. Once testing results are received, the normal infants can be given breast milk or commercially available infant formula. Since 1.1 g of protein per 100 ml of formula having 20 kcal/oz have provided normal growth and serum indicators of protein nutritional status, such formula with 1.3–1.6 g protein per 100 ml (1.9 to 2.7 g protein per 100 kcal) can be continued even after the metabolic evaluation in normal infants. This suggests a daily intake of 2.4 to 3.0 g protein per kg of body weight, which exceeds the protein requirement estimated by the factorial approach (Raiha et al. Protein Nutrition During infancy, *Ped Clin North Amer,* 1995; 42: 745). However, the present invention is intended to be used to reduce the severity of metabolic disorder and not as a method of treating inborn metabolic disorders. Infants diagnosed with metabolic disorders can be given conventional formula designed for the specific disorder with which they are diagnosed. However, some metabolic disorders treated by reduced protein intake can be continued on the composition described herein.

More specifically, the present invention is used to treat infants from day zero to the day the final report of diagnostic studies for inborn error of metabolism is received; preferably from day zero to day fourteen; more preferably from day zero to day ten; and more preferably, from day zero to day seven.

Diseases Caused By Inborn Errors of Metabolism

Examples of various disease conditions resulting from inborn errors of metabolism that can be treated with the method of the present invention include Maple Syrup Urine Disease, Urea Cycle Disorders, and Organic Acid Metabolism Disorders.

Maple Syrup Urine Disease

Maple Syrup Urine Disease (MSUD) or branched chain ketoaciduria is an autosomal recessive metabolic disorder of panethnic distribution. The neonatal screening for MSUD is performed either by the Guthrie bacterial inhibition assay or by tandem mass spectrometry (MS/MS). The worldwide incidence of MSUD is estimated to be approximately 1:185,000. MSUD is caused by a deficiency in activity of the branched chain α-keto acid dehydrogenase (BCKAD) complex. This metabolic block results in the accumulation of the branched chain amino acids (BCAA), such as leucine, isoleucine and valine and the corresponding branched chain α-keto acids (BCKA). These infants appear normal at birth, but after a few days they develop a poor appetite, become apathetic and lethargic, and then manifest neurologic signs, such as loss of normal reflexes. Alternating periods of atonia and hypertonicity appear, followed by convulsions and respiratory irregularities. MSUD is most often accompanied by a characteristic odor in the urine, perspiration and earwax. If left untreated, the disease is almost always fatal in the first weeks of life.

Severe MSUD is characterized by plasma BCAA concentrations of:

about ≧500 micromoles/dL leucine about ≧100 micromole/dL isoleucine and about ≧100 micromole/dL valine;

and plasma BCKA concentrations of:

about 60 to 460 micromoles/dL α-ketoisocaproic acid, about 20 to 150 micromole/dL α-keto-β-methylvaleric acid, and about 2 to 35 micromole/dL α-ketoisovaleric acid Preventing severe MSUD in a patient means that these levels are not reached in a patient treated with the method of the present invention and later diagnosed with MSUD.

Moderate MSUD is characterized by moderately elevated BCAA; for instance, about 60 to 100 micromoles/dL instead of ≧100 micromoles/dL leucine.

In classic MSUD at two weeks after birth, the patient is placed on an amino acid diet from which the branched chain amino acids are omitted, and supplements of carbohydrates, lipids, vitamins and minerals are added. When the plasma levels of BCAA are reduced to normal range these amino acids are added to the diet in highly restricted manner to maintain the plasma levels within normal or slightly above normal limits.

Urea Cycle Disorders

The urea cycle consists of a series of five biochemical reaction and serves two purposes: (1) it incorporates nitrogen atoms not retained for net biosynthetic purposes into which serves as a waste nitrogen product, in order to prevent the accumulation of toxic nitrogenous compounds; and (2) it contains several of the biochemical reactions required for the de novo biosynthesis and degradation of arginine. Interruptions in the metabolic pathway for urea synthesis are caused by the deficiency or inactivity of any one of several enzymes involved in specific steps in the cascade. A defect in the ureageneic pathway has two consequences: arginine becomes an essential amino acid (except in arginase deficiency, where the enzyme defect results in a failure of degradation of arginine) and nitrogen atoms accumulate in a variety of molecules the pattern of which varies according to the specific enzymatic defect although plasma levels of ammonium and glutamine are increased in all urea cycle disorders not under metabolic control. Urea cycle disorders include: (a) carbamyl phosphate synthetase deficiency (CPSD), (b) N-acetyl glutamate synthetase deficiency, (c) ornithine transcarbamylase deficiency (OTCD), (d) argininosuccinic acid synthetase deficiency (ASD), (e) argininosuccinate lyase deficiency (ALD), and (f) arginase deficiency.

Except ornithine transcarbamylase deficiency, which is an X-linked generic disorder, urea cycle disorders are inherited by autosomal recessive fashion. Newborn screening using MS/MS technology can detect argininosuccinate synthetase deficiency (citrullinemia), argininosuccinate lyase deficiency (argininosuccinicaciduria), arginase deficiency and hyperammonemia-hyperornithinemia-homocitrullinemia syndrome (HHH). Once hyperammonemia is identified, other types of urea cycle disorders can also be diagnosed by biochemical and molecular methods. Great variability within and among these disorders is due to the difference of mutational characteristics.

Each of these diseases represents a defect in the biosynthesis of one of the normally expressed enzymes of the urea cycle and is characterized by signs and symptoms induced by the accumulation of precursors of urea, principally ammonium and glutamine. The common pathologic sequlae of these clinical disorders is the extreme elevation of the plasma ammonia level.

Severe urea cycle disorders are characterized by plasma ammonia level of about 2,000 to about 2,500 micrograms/dL ammonia and the patient requires a medical emergency for artificial respiration and hemodialysis in addition to the provision of alternative metabolism of ammonia. Preventing severe urea cycle disorders means that these levels are not reached in a patient treated with the method of the present invention and later diagnosed with a urea cycle disorder.

Moderate urea cycle disorders are characterized by plasma ammonia levels less than about 500 micromoles/dL and may not require such aggressive therapy. Thus, detection of hyperammonemia is most important for early diagnosis and effective treatment. Typically associated with this increase in ammonia buildup are acute episodes of vomiting, lethargy, convulsions and abnormal liver enzyme levels. Exposure to high levels of plasma ammonia is fatal typically following a period of lethargy, convulsions and coma. Even treated, protracted severe hyperammonemia leads to mental and physical retardation.

For fetuses at risk, antenatal diagnosis is available by a number of methods, particular to each disease, including enzyme analysis of fibroplasts cultured from aminocytes, in utero liver biopsy, and DNA techniques. All of these disorders respond to some degree to restriction of protein intake. Acute episodes are usually precipitated by an increased protein intake, an infection or any incident that leads to a negative nitrogen balance. Treatment requires a restriction of dietary protein intake and activation of other pathways of waste nitrogen synthesis and excretion.

Organic Acid Metabolic Disorders

The disorders of propionate metabolism, methylmalonic acidemia (MMA) and propionic acidemia (PA), are the most common disorders of organic acid metabolism. These disorders usually present in the neonatal period or early infancy with vomiting, lethargy and metabolic acidosis, which may progress to coma and death. The mainstay of treatment of PA and MMA is a diet restricted in isoleucine, methionine, threonine, and valine. An inadequate isoleucine, methionine, threonine and valine intake leads to poor growth with chronic malnutrition, a serious complication of the organic acidemias.

Propionic acidemia (PA) is a deficiency or inactivity of propionylcoenzyme A carboxylase and results in the accumulation of propionyl-coenzyme A and propionic acid. Clinically, patients present with vomiting, dehydration, lethargy and hypotonia in early infancy and are found to have ketonuria and metabolic acidosis. Severe PA is characterized by plasma propionic acid concentration of about 540 micromoles/dL, a value that is about 100 times more than the normal value. Normal dietary protein is toxic to these patients; toxicity is caused by the presence of excess metabolites of the amino acids: isoleucine, methionine, threonine and valine. Preventing severe PA means that these levels are not reached in a patient treated with the method of the present invention and later diagnosed with PA.

After diagnosis, infants with this disorder respond well to dietary restrictions of isoleucine, methionine, threonine and valine particularly in the presence of adequate energy and protein equivalent.

Methylmalonicacidemia (MMA) results from an accumulation of methylmalonyl coenzyme A and methylmalonic acid as a result of inactivity of one of two enzymes sites: conversion of methylmalonic A to succinyl coenzyme A by methylmalonyl coenzyme A mutase or enzymes involved in the synthesis of adenosylcobalamin. As with PA, patients with MMA generally present with vomiting, dehydration, lethargy and hypotonia in early infancy and are found to have ketonuria and metabolic ketoacidosis.

Severe MMA is characterized by:

about <6.9 blood pH values about <5 mEq/L plasma bicarbonate concentration; and about >290 micromoles/dL plasma methylmalonate concentration.

Preventing severe MMA means that these levels are not reached in a patient treated with the method of the present invention and later diagnosed with MMA.

After diagnosis, about half of the patients having this metabolic defect have responded to the administration of large amounts of vitamin B12. The B12 responsive type is due to a defect in the metabolism of 5' deoxyadenosyl-B12, while the B12 non-responsive type is the result of an alteration in the methylmalonyl-coenzyme A mutase.

Post-diagnosis treatment consists of restricting isoleucine, methionine, threonine and valine intakes and alkali therapy for the episodes of acidosis. Typically nutritional support requires severe limitation of the recognized propionate precursor amino acids: isoleucine, valine, methionine and threonine. Catabolism of odd-chain fatty acids, cholesterol and bacterial fermentation in the gut are also recognized as sources of propionate, and catabolism of thymine as a source of methylmalonate accumulation.

MS/MS technology is used for newborn screening of organic acid disorders. In addition to PA and MMA, other organic acid disorders, such as 2-methylbutyryl coenzyme A dehydrogenase deficiency, 3-hydroxy-3-methylglutaryl coenzyme A lyase deficiency (HMG), 3-methylcrotonyl coenzyme A carboxylase deficiency, 3-methylglutaconyl coenzyme A hydratase deficiency, 5-oxoprolinuria, glutaric academia type I, isobutyryl coenzyme A dehydrogenase deficiency, isovaleric academia, malonic aciduria, mitochondrial acetoacetyl coenzyme A thiolase deficiency, and multiple carboxylase deficiency, can be detected by this method. However, severe metabolic deterioration due to ketoacidosis and hyperammonemia during the early newborn period is usually seen in PA and MMA.

The time of onset and the severity of illness of the metabolically abnormal infant after birth are dependent on the nature of metabolic block and the amount of available amino acids and protein. MSUD and other branched chain amino acid disorders accumulate $\alpha$-ketoacids derived from BCAA, such as leucine, isoleucine, and/or valine. On the other hand, urea cycle disorder is related to the metabolism of almost all amino acids, leading to the accumulation of glutamine, the precursor of ammonia.

The accumulation of propionic acid and methylmalonic acid is mainly through the oxidation of isoleucine, valine, methionine, and threonine, causing profound acidosis. Unless, there is a means to activate the deficient enzyme activity or provide an alternative pathway, the accumulation of metabolites is extremely fast leading to the sudden development of severe hyperammonemia and/or metabolic acidosis. Such rapid development of metabolite accumulation is caused by transamination of amino acids, which is closely correlated with the amount of protein intake. For this reason, the prevention and long-term therapeutic measures of recurrent life-threatening hyperammonia and ketoacidosis are dependent on protein restriction.

Method of Testing for Inborn errors of Metabolism

With the exception of few disorders, most states perform the screening study for each infant. Typically, the specimen is collected approximately 24 hours after birth. The result of the studies is available within approximately two weeks after the test.

Composition

The infant formula of the present invention contains (a) protein (b) carbohydrate, (c) fat and (d) vitamins and minerals.

The infant formula of the present invention contains "a minimum level of protein required for normal growth," which is a level of protein up to about 1.8 grams protein per 100 kcal (or about 1.22 g protein per 100 ml) of a composition having 20 kcal per ounce. Preferably, the level of protein is between about 1.3 and about 1.8 grams protein per 100 kcal (or about 0.9 to about 1.22 g protein per 100 ml) of a composition having 20 kcal per ounce. Most preferably, the level of protein is between about 1.3 and about 1.6 grams protein per 100 kcal (or about 0.9 to about 1.08 g protein per 100 ml) of a composition having 20 kcal per ounce.

The protein can be any supplied in any conventional form such as casein, salts of casein (e.g. potassium caseinate), whey protein concentrate, soybean protein isolate, cow's milk protein, or hydrolyzed whey, or soy protein. Preferably whey and casein are used. Preferably the whey: casein ratio is 60:40 and 70:30. The whey can be prepared to have reduced allergenicity using conventional techniques such as described in U.S. Pat. No. 4,879,131. The whey can also be demineralized for example by electrodialysis or ultrafiltration.

The formula of the present invention provides approximately 40–50% of its total non-protein calories as carbohydrate. The source of carbohydrate can be supplied in any conventional form including both simple and complex forms. Preferably, the carbohydrate is provided in simple form. Simple carbohydrates include lactose, sucrose, and corn syrup solids. Complex carbohydrates include starches. Most preferably, the source of carbohydrate is lactose. Alternatively, glucose or sucrose can be used.

The formula of the present invention contains 45–55% of its total calories as fat. The fat can be supplied in any conventional form including saturated fats, monounsaturated fats (MUFA), polyunsaturated fats (PUFA) or a mixture thereof. Preferably the fat is provided as ⅓ saturated fat, ⅓ MUFA and ⅓ PUFA. Saturated fats include butyric, valeric, caproic, caprylic, decanoic, lauric, myristic, palmitic, steraic, arachidic, behenic and lignoceric. MUFAs include palmitoleic, oleic, claidic, vaccenic and erucic. PUFAs include linoleic, $\alpha$-linolenic (18:3), $\gamma$-linoleic (1 8:2), aracadonic (20:4), eicosopenanoate (20:5) and decosodexanoic (22:6). Preferably, PUFA is supplied as a $\alpha$-linolenic and linoleic.

An exemplary formulation includes:

|  | Preferred source | Amount |
| --- | --- | --- |
| Protein | Cow milk protein and dimineralized whey | 1.3–1.6 g/100 kcal |
| Fat | Cow milk (lipids), soy or coconut lipids. | 3.0–4.0 g/100 ml |
| Carbohydrate | Cow milk (lactose), glucose or sucrose. | 7.0–10.0 g/100 ml |

Results of Treatment

The present invention postpones the onset of the infantile type acute hyperammonemia and metabolic acidosis and the onset experienced is a less severe degree compared with full-blown biochemical and clinical abnormalities. Typically, the severity is reduced to a level such that the metabolically abnormal infant is capable of responding to treatment with medical foods for use in the nutritional support of an infant having the inherited metabolic disorder with or without other interventions. The present invention further prevents irreversible damage, such as permanent damage of the central nervous system mental retardation, coma and death, to undiagnosed metabolically abnormal infants.

What is claimed is:

1. A method of reducing severity and delaying onset of hyperammonemia and metabolic acidosis in an infant having an inherited metabolic disorder comprising administering to a newborn during a time prior to diagnosis of the inherited metabolic disorder a composition comprising about 20 kcal per ounce and up to about 1.8 g protein per 100 kcal of said composition.

2. The method of claim 1 wherein said composition has about 20 kcal per ounce and between about 1.3 g and about 1.6 g protein per 100 kcal of said composition.

3. The method of claim 1 wherein said time prior to diagnosis is between about day 0 and up to about day 14 of life.

4. The method of claim 1 wherein said time prior to diagnosis is between about day 0 to day 10 of life.

5. The method of claim 1 wherein said time prior to diagnosis is between about day 0 to day 7 of life.

6. The method of claim 1 wherein the infant is a normal infant or has a metabolic disorder.

7. A method of reducing severity and delaying onset of hyperammonemia and metabolic acidosis in an infant having an inherited metabolic disorder selected from the group consisting of maple syrup urine disease, a urea cycle disorder and an organic acid metabolic disorder comprising administering to a population of undiagnosed newborn infants from day 0 to 14 a composition comprising 20 kcal per ounce and less than about 1.8 g protein per 100 kcal.

8. The method of claim 7 wherein said composition comprises between about 1.3 and about 1.6 g protein per 100 kcal.

* * * * *